United States Patent [19]
Fukuda et al.

[11] Patent Number: 6,087,500
[45] Date of Patent: Jul. 11, 2000

[54] METHODS FOR PRODUCING PYRIMIDINE COMPOUNDS

[75] Inventors: Kenzo Fukuda; Masataka Hatanaka; Takahiro Makabe; Kenichi Ishii, all of Onoda, Japan

[73] Assignee: Nissan Chemical Industries, Ltd., Tokyo, Japan

[21] Appl. No.: 09/147,260

[22] PCT Filed: May 7, 1997

[86] PCT No.: PCT/JP97/01534

§ 371 Date: Nov. 13, 1998

§ 102(e) Date: Nov. 13, 1998

[87] PCT Pub. No.: WO97/43265

PCT Pub. Date: Nov. 20, 1997

[30] Foreign Application Priority Data

| | | | |
|---|---|---|---|
| May 20, 1996 | [JP] | Japan | 8-125109 |
| May 21, 1996 | [JP] | Japan | 8-125463 |
| May 16, 1996 | [JP] | Japan | 8-121365 |
| Jun. 11, 1996 | [JP] | Japan | 8-147746 |
| Jul. 19, 1996 | [JP] | Japan | 8-190573 |
| Mar. 31, 1997 | [JP] | Japan | 9-080291 |

[51] Int. Cl.$^7$ .................. C07D 239/28; C07D 239/30

[52] U.S. Cl. .................................................. 544/320

[58] Field of Search ................................. 544/320

[56] References Cited

FOREIGN PATENT DOCUMENTS 391714   9/1965   Switzerland.

OTHER PUBLICATIONS

Baldwin et al. Condenstion reaction of chloroformylsulfur . . . J. Chem. Soc. Perkins Trans. 375–377, 1975.

*Primary Examiner*—Mukund J. Shah
*Assistant Examiner*—Venkataraman Balasubramanian
*Attorney, Agent, or Firm*—Oblon, Spivak, McClelland, Maier & Neustadt, P.C.

[57] ABSTRACT

A method for producing 2-amino-4,6-dimethoxypyrimidine, wherein 2-amino-5-chloro-4,6-dimethoxypyrimidine produced by reacting heptachloropropane or hexachloropropene and guanidine with methanol in the presence of a base, or by reacting 2-amino-4,5,6-trichloropyrimidine with methanol in the presence of a base, is used; and a method for producing 2-amino-4,6-dimethoxypyrimidine, characterized by reacting hexachloropropane or pentachloropropene and guanidine with methanol in the presence of a base.

9 Claims, No Drawings

METHODS FOR PRODUCING PYRIMIDINE COMPOUNDS

TECHNICAL FIELD

The present invention relates to methods for producing 2-amino-4,6-dimethoxypyrimidine useful as an intermediate for drugs and pesticides, particularly as an intermediate for herbicides, its starting material 2-amino-5-chloro-4,6-dimethoxypyrimidine and its intermediate 2-amino-4,5-dichloro-6-methoxypyrimidine.

BACKGROUND ART

2-Amino-4,6-dimethoxypyrimidine and its derivatives are a group of compounds which are useful as intermediates for various fine chemicals such as biologically active substances, like drugs and pesticides as well as important intermediates for sulfonylurea herbicides described in JP-A-59-122488, JP-A-61-210084 and JP-A-60-208977.

2-Amino-4,5-dichloro-6-methoxypyrimidine is useful, for example, for producing phenylaminopyrimidine compounds described in JP-A-60-51177 and JP-A-61-15877.

As a method for producing 2-amino-4,6-dimethoxypyrimidine, many methods have been known. For example, JP-B-1-211411 discloses a production method by reacting bisimidate obtained from malononitrile with cyanogenchloride. And JP-A-64-16770 discloses a method for producing 2-amino-4,6-dimethoxypyrimidine by reacting 2-amino-4,6-dihydroxypyrimidine with phosphorous oxychloride in the presence of an organic base to prepare 2-amino-4,6-dichloropyrimidine (J. Amer. Chem. Soc., vol. 73, page 3011 (1951)), followed by methoxylation with a metal hydroxide and methanol.

On the other hand, as a method for producing 2-amino-5-chloro-4,6-dimethoxypyrimidine, a method to chlorinate 2-amino-4,6-dimethoxypyrimidine has been known as described in J. Chem. Soc. Perkin Trans. 1, page 375 (1975).

However, with the conventional methods, various types of by-products are generated with large quantities, and improvement is therefore required. And, 2-amino-4,5-dichloro-6-methoxypyrimidine and methods for its production have not been known at all.

DISCLOSURE OF THE INVENTION

The present inventors have conducted extensive studies to overcome the above problems, and the present invention has been accomplished. Namely, the present invention provides a method for producing 2-amino-4,6-dimethoxypyrimidine (hereinafter referred to as compound (I)), characterized by reacting 2-amino-5-chloro-4,6-dimethoxypyrimidine (hereinafter referred to as compound (II)) with a hydrogen donor using a metal catalyst selected from nickel catalyst, palladium catalyst and platinum catalyst, in the presence of a base if necessary (hereinafter referred to as production method A), a method for producing compound (I), using compound (II) produced by reacting 1,1,1,2,2,3,3-heptachloropropane, 1,1,1,2,3,3,3-heptachloropropane or hexachloropropene with guanidine or its salt, in the presence of an alkali metal hydroxide, an alkaline earth metal hydroxide, an alkali metal methoxide or an alkaline earth metal methoxide (hereinafter referred to as production method A1), a method for producing compound (I), using compound (II) produced by reacting 2-amino-4,5-dichloro-6-methoxypyrimidine (hereinafter referred to as compound (III)) with methanol, in the presence of an alkali metal hydroxide, an alkaline earth metal hydroxide, an alkali metal methoxide or an alkaline earth metal methoxide (hereinafter referred to as production method A2), a method for producing compound (II), using compound (III) produced by reacting 2-amino-4,5,6-trichloropyrimidine (hereinafter referred to as compound (IV)) with methanol, in the presence of an alkali metal carbonate, an alkali metal hydrogencarbonate, an alkaline earth metal carbonate or an alkaline earth metal hydrogencarbonate (hereinafter referred to as production method A3), a method for producing compound (I), using compound (II) produced by reacting compound (IV), with methanol, in the presence of an alkali metal hydroxide, an alkaline earth metal hydroxide, an alkali metal methoxide or an alkaline earth metal methoxide (hereinafter referred to as production method A4), a method for producing compound (I), characterized by reacting 1,1,1,3,3,3-hexachloropropane or 1,1,3,3,3-pentachloropropene with guanidine or its salt, in the presence of an alkali metal hydroxide, an alkaline earth metal hydroxide, an alkali metal methoxide or an alkaline earth metal methoxide (hereinafter referred to as production method B), a method for producing compound (II), characterized by reacting 1,1,1,2,2,3,3-heptachloropropane, 1,1,1,2,3,3,3-heptachloropropane or hexachloropropene with guanidine or its salt, in the presence of an alkali metal hydroxide, an alkaline earth metal hydroxide, an alkali metal methoxide or an alkaline earth metal methoxide (hereinafter referred to as production method C), a method for producing compound (II), characterized by reacting compound (III) with methanol, in the presence of an alkali metal hydroxide, an alkaline earth metal hydroxide, an alkali metal methoxide or an alkaline earth metal methoxide (hereinafter referred to as production method D), a method for producing compound (II), characterized by reacting compound (IV) with methanol, in the presence of an alkali metal hydroxide, an alkaline earth metal hydroxide, an alkali metal methoxide or an alkaline earth metal methoxide (hereinafter referred to as production method E), a method for producing compound (II), characterized by reacting compound (IV) with methanol, in the presence of an alkali metal carbonate, an alkali metal hydrogencarbonate, an alkaline earth metal carbonate or an alkaline earth metal hydrogencarbonate (hereinafter referred to as production method F). And compound III is a novel compound.

BEST MODE FOR CARRYING OUT THE INVENTION

Hydrogenolysis in production method A can be conducted by using nickel catalyst, palladium catalyst or platinum catalyst. And, the reaction can be conducted in the coexistence of an organic base or an inorganic base as a hydrochloric acid scavenger.

As the organic base or the inorganic base, ammonia, triethylamine, pyridine, ammonium formate, sodium formate, potassium formate, sodium acetate, potassium acetate, sodium hydroxide, potassium hydroxide, sodium carbonate and potassium carbonate are preferred. The amount of the organic base or the inorganic base is preferably from 1 to 10 mol, more preferably from 1 mol to small excess, per mol of 2-amino-5-chloro-4,6-dimethoxypyrimidine.

As the hydrogen donor, hydrogen gas, sodium borohydride and sodium formate are preferred, and hydrogen gas is particularly preferred.

The reaction pressure is preferably from reduced pressure to 100 atm, more preferably from atmospheric pressure to 10 atm.

The reaction temperature is preferably from 0 to 300° C., more preferably from 20 to 150° C.

The reaction time is preferably from one minute to 50 hours, more preferably from 30 minutes to 10 hours.

The solvent to be used for the present reaction is not particularly limited as long as it is inert to the reaction. It includes, for example, water, ethers such as tetrahydrofuran, diethyl ether, diethylene glycol diethyl ether and 1,4-dioxane, aliphatic hydrocarbons such as hexane, heptane, octane, nonane and decane, aromatic hydrocarbons such as benzene, toluene, xylene, and tetrahydronaphthaline, alcohols such as methanol, ethanol, propanol and ethylene glycol, cellosolves such as methoxyethanol and ethoxyethanol, fatty acids such as formic acid, acetic acid and propionic acid, and their mixed solvents.

As a treatment method of reaction solution, the reaction products may be purified or isolated by e.g. extraction, distillation, recrystallization, or chromatography separation, if necessary, after the solvent is removed by distillation.

1,1,1,3,3,3-Hexachloropropane or 1,1,3,3,3-pentachloropropene to be used as a starting material in production method B can be easily produced by known methods. For example, 1,1,1,3,3,3-hexachloropropane can be produced by the method disclosed in J. Mol. Catal. vol. 77, page 51 (1992), and 1,1,3,3,3-pentachloropropene can be easily produced by the method disclosed in Chem. Ber. vol. 100, page 3716 (1967).

As the alkali metal hydroxide or the alkaline earth metal hydroxide, potassium hydroxide, sodium hydroxide, barium hydroxide, magnesium hydroxide and calcium hydroxide are preferred, and sodium hydroxide is particularly preferred.

As the alkali metal methoxide or the alkaline earth metal methoxide, lithium methoxide, sodium methoxide, potassium methoxide, magnesium methoxide, calcium methoxide, barium methoxide and strontium methoxide are preferred, and sodium methoxide is particularly preferred. And these may be simple substances or in the form of methanol solutions.

The amount of the methoxide is preferably from 2 to 15 mol, more preferably from 4 to 10 mol, per mol of 1,1,1,3,3,3-hexachloropropane or 1,1,3,3,3-pentachloropropene.

The reaction temperature is preferably from −70 to 200° C., more preferably from 0 to 100° C.

The solvent is not particularly limited as long as it is inert to the reaction. It includes, for example, water, ethers such as tetrahydrofuran, diethyl ether diethylene glycol dimethyl ether and 1,4-dioxane, aliphatic hydrocarbons such as hexane, heptane, octane, nonane and decane, aromatic hydrocarbons such as benzene, toluene, xylene, chlorobenzene, dichlorobenzene and tetrahydronaphthalene, nitriles such as acetonitrile, ketones such as acetone and methyl isobutylketone, polar solvents such as N,N-dimethylformamide, N,N-dimethylacetamide, dimethyl sulfoxide and 1,3-dimethyl-2-imidazolidinone, methanol, and their mixed solvents.

The present reaction can be conducted either under atmospheric pressure or under elevated pressure.

In the present invention, compound (I) can be obtained by reacting a guanidine salt with a methoxide in the presence of a solvent to liberate guanidine, then adding 1,1,1,3,3,3-hexachloropropane or 1,1,3,3,3-pentachloropropene thereto, or by reacting a mixture of a guanidine salt and 1,1,1,3,3,3-hexachloropropane or 1,1,3,3,3-pentachloropropene with a methoxide added in the presence of a solvent, then adding water and extracting the reaction products with an organic solvent, followed by crystallizing and washing.

As the alkali metal hydroxide or the alkaline earth metal hydroxide to be used in the production method C, potassium hydroxide, sodium hydroxide, barium hydroxide, magnesium hydroxide and calcium hydroxide are preferred, and sodium hydroxide is particularly preferred. As the alkali metal methoxide or the alkaline earth metal methoxide, lithium methoxide, sodium methoxide, potassium methoxide, magnesium methoxide, calcium methoxide, barium methoxide and strontium methoxide, barium methoxide and strontium methoxide are preferred, and sodium methoxide is particularly preferred. They can be used either as simple substances or in the form of methanol solutions.

The alkali metal methoxide or the alkaline earth metal methoxide can be produced by adding sodium hydride, potassium hydride, lithium hydride, metal sodium, metal potassium, metal lithium, butyl lithium or lithium diisopropylamide into methanol.

The amount of methoxide is preferably from 2 to 10 mol, more preferably from 4.0 to 7.0 mol, per mol of 1,1,1,2,2,3,3-heptachloropropane, 1,1,1,2,3,3,3-heptachloropropane or hexachloropropene.

As the guanidine salt, not only inorganic acid salts such as hydrochloride, nitrate, sulfate and carbonate, but organic acid salts can be used as well. Its amount is usually preferably from 0.5 to 10 mol, more preferably from 0.8 to 2 mol, per mol of heptachloropropane or hexachloropropene.

The reaction temperature, is preferably from −10 to 200° C., more preferably from 20 to 150° C.

The solvent is not particularly limited as long as it is inert to the reaction. It includes, for example, water, ethers such as tetrahydrofuran, diethyl ether diethylene glycol dimethyl ether and 1,4-dioxane, aliphatic hydrocarbons such as hexane, heptane, octane, nonane and decane, aromatic hydrocarbons such as benzene, toluene, xylene, chlorobenzene, dichlorobenzene and tetrahydronaphthalene, nitrites such as acetonitrile, ketones such as acetone and methyl isobutylketone, polar solvents such as N,N-dimethylformamide, N,N-dimethylacetamide, dimethyl sulfoxide and 1,3-dimethyl-2-imidazolidinone, methanol, and their mixed solvents.

The present reaction can be conducted either under atmospheric pressure or under elevated pressure.

In the present invention, compound (II) can be obtained in good yield by reacting a guanidine salt with a methoxide in the presence of a solvent to liberate guanidine, then adding 1,1,1,2,2,3,3-heptachloropropane, 1,1,1,2,3,3,3-heptachloropropane or hexachloropropene thereto, or by reacting a guanidine salt and 1,1,1,2,2,3,3-heptachloropropane, 1,1,1,2,3,3,3-heptachloropropane or hexachloropropene with a methoxide in the presence of a solvent, then adding water and extracting the reaction products with an organic solvent, followed by crystallizing and washing.

As the alkali metal hydroxide, the alkaline earth metal hydroxide, the alkali metal methoxide or the alkaline earth metal methoxide to be used in production method D, sodium methoxide, potassium hydroxide, sodium hydroxide, barium hydroxide, magnesium hydroxide and calcium hydroxide are preferred, and sodium hydroxide is particularly preferred in view of reactivity and economy. And, they can be used as a mixture of at least two bases.

The amount of base is preferably from none to 10 mol, more preferably from 1 to 3 mol, per mol of compound (III).

The reaction pressure is preferably from reduced pressure to 100 atm, more preferably from atmospheric pressure to 10 atm.

The reaction temperature is preferably from 0 to 300° C., more preferably from 20 to 150° C.

The reaction time is preferably from 10 minutes to 50 hours, more preferably from 30 minutes to 10 hours.

The solvent is not particularly limited as long as it is inert to the reaction. It includes, for example, water, ethers such as tetrahydrofuran, diethyl ether, diethylene glycol dimethyl ether and 1,4-dioxane, aliphatic hydrocarbons such as hexane, heptane, octane, nonane, and decane, aromatic hydrocarbons such as benzene, toluene, xylene and tetrahydronaphthalene, methanol and their mixed solvents.

As a treatment method of the reaction solution, the solvent is removed by distillation, if necessary, and then, water is added to precipitate crystals followed by washing and filtration to obtain the desired product. Or, after the solvent is removed, 2-amino-5-chloro-4,6-dimethoxypyrimidine can be purified or isolated by extraction, recrystallization and chromatography separation of the reaction product.

As the alkali metal hydroxide, the alkaline earth metal hydroxide, the alkali metal methoxide or the alkaline earth metal methoxide to be used in production method E, sodium methoxide, potassium hydroxide, sodium hydroxide, barium hydroxide, magnesium hydroxide and calcium hydroxide are preferred, and sodium hydroxide is particularly preferred in view of reactivity and economy. And, they can be used as a mixture of at least two bases.

The amount of base is preferably from none to 10 mol, more preferably from small excess to 2 mol, per mol of compound (IV).

The reaction pressure is preferably from reduced pressure to 100 atm, more preferably from atmospheric pressure to 10 atm.

The reaction temperature is preferably from 0 to 300° C., more preferably from 20° C. to 150° C.

The reaction time is preferably from 10 minutes to 50 hours, more preferably from 30 minutes to 10 hours.

The solvent is not particularly limited as long as it is inert to the reaction, it includes, for example, water, ethers such as tetrahydrofuran, diethyl ether, diethylene glycol diethyl ether and 1,4-dioxane, aliphatic hydrocarbons such as hexane, heptane, octane, nonane and decane, aromatic hydrocarbons such as benzene, toluene; xylene and tetrahydronaphthaline, methanol and their mixed solvents.

As a treatment method of the reaction solution, the solvent is removed by distillation if necessary, and then the reaction product is subjected to e.g. extraction, recrystallization or chromatography separation to purify or isolate the compound (I). Compound (IV) which is a starting material of the present invention, can be produced by known methods [for example, J. Amer. Chem. Soc., vol. 72, page 4271 (1950)].

As the alkali metal carbonate or the alkali metal hydrogencarbonate to be used in the production method F, sodium hydrogencarbonate, potassium hydrogencarbonate, sodium carbonate and potassium carbonate are preferred, and sodium carbonate is particularly preferred in view of reactivity and economy. As the alkaline earth metal carbonate or the alkaline earth metal hydrogencarbonate, magnesium carbonate, calcium carbonate, barium carbonate, magnesium hydrogencarbonate and calcium hydrogencarbonate are preferred. It is possible to use a mixture of at least two bases.

The conditions of production method F are in accordance with conditions of production method E.

These production methods may be used as combined as production methods A1, A2, A3 and A4.

EXAMPLES

Now, the present invention will be described in detail with reference to Examples. However, the present invention is not restricted thereto.

Production Method A

Example A-1

3.03 g (16 mmol) of compound (II), 0.5 g of active carbon-supported 10% palladium [product of NE Chemcat (water content 50%)], 9.8 g of potassium acetate and 300 g of acetic acid were put into a reaction flask substituted by nitrogen, hydrogen gas was supplied under atmospheric pressure, and reaction was conducted at a temperature of 100° C. for 6 hours. The disappearance of 2-amino-5-chloro-4,6-dimethoxypyrimidine was confirmed by liquid chromatography, acetic acid was distilled off from the reaction mixture, 20 g of methylisobutylketone was added thereto, followed by washing with water. The organic layer was dried over anhydrous sodium sulfate, and the solvent was distilled off to obtain 2.38 g (15.4 mmol) (yield 96%) of compound (I).

Example A-2

3.03 g (16 mmol) of compound (II) and 0.5 g of active carbon-supported 10% palladium [product of NE Chemcat (water content 50%)], 9.8 g of potassium acetate and 300 g of acetic acid were put into a reaction flask substituted by nitrogen, and stirred well at a temperature of 25° C. into which hydrogen gas was supplied under atmospheric pressure, and reaction was conducted for 24 hours. The production of 31% of compound (I) was confirmed by liquid chromatography.

Example A-3

3.03 g (16 mmol) of compound (II), 0.5 g of active carbon-supported 10% palladium [product of NE Chemcat (water content 50%)], 9.8 g of potassium acetate and 300 g of methoxy ethanol were put into a reaction flask substituted by nitrogen, hydrogen gas was supplied under atmospheric pressure and reaction was conducted at a temperature of 120° C. for 24 hours. The production of 75% of compound (I) was confirmed by liquid chromatography.

Production Method B 1.00 g (10.5 mmol) of guanidine hydrochloride was added to a mixture of 3.58 g (63.0 mmol) of 95% sodium methoxide and 10.0 g of diethylene glycol dimethyl ether, and the reaction was conducted at a temperature of 60° C. for one hour. 2.25 g (10.5 mmol) of 1,1,3,3,3-pentachloropropene was dropwise added thereto at a temperature of at highest 10° C., and the reaction was conducted for one hour. Then, 20 g of methylisobutylketone and 20 g of water were added, and the organic layer was separated. The organic layer was washed with water, and dried over anhydrous sodium sulfate, and the solvent was distilled off, whereupon precipitated crystals were washed with heptane, to obtain 0.34 g (yield 17%) of compound (I).

Production Method C

Example C-1

14.1 g (73.3 mmol) of 28% sodium methoxide (methanol solution) was dropwise added to a mixture of 1.00 g (10.5 mmol) of guanidine hydrochloride, 2.99 g (10.5 mmol) of 1,1,1,2,2,3,3-heptachloropropane and 3.0 g of methanol over a period of one hour under reflux. The reaction was conducted further for one hour, then methanol was distilled off, 20 g of methylisobutylketone and 20 g of water were added thereto, and the organic layer was separated. The organic layer was dried over anhydrous sodium sulfate, the solvent was distilled off and precipitated crystals were washed with heptane to obtain 0.44 g (yield 22%) of compound (II).

Example C-2

14.1 g (73.3 mmol) of 28% sodium methoxide (methanol solution) was dropwise added to a mixture of 1.00 g (10.5 mmol) of guanidine hydrochloride, 2.99 g (10.5 mmol) of 1,1,1,2,3,3,3-heptachloropropane and 3.0 g of methanol under reflux over a period of one hour. The reaction was conducted further for one hour, the methanol was distilled off, 20 g of methylisobutylketone and 20 g of water were added, and the organic layer was separated. The organic layer was dried over anhydrous sodium sulfate, the solvent was distilled off and precipitated crystals were washed with heptane to obtain 0.50 g (yield 25%) of compound (II).

Example C-3

12.1 g (62.8 mmol) of 28% sodium methoxide (methanol solution) was dropwise added to a mixture of 1.00 g (10.5 mmol) of guanidine hydrochloride, 2.60 g (10.5 mmol) of hexachloropropene and 3.0 g of methanol over a period of one hour under reflux. The reaction was conducted further for one hour, the methanol was distilled off, 20 g of methylisobutylketone and 20 g of water were added, and the organic layer was separated. The organic layer was dried over anhydrous sodium sulfate, the solvent was distilled off and precipitated crystals were washed with heptane to obtain 0.60 g (yield 30%) of compound (II).

Example C-4

3.00 g (31.4 mmol) of guanidine hydrochloride was added to 6.06 g (31.4 mmol) of 28% sodium methoxide (methanol solution), then 2.60 g (10.5 mmol) of hexachloropropene was dropwise added thereto over a period of one hour under reflux. One hour later, 10.1 g (52.3 mmol) of 28% sodium methoxide (methanol solution) was dropwise added thereto over a period of one hour. The reaction was conducted for one hour and then methanol was distilled off, 20 g of methylisobutylketone and 20 g of water were added, and the organic layer was separated. The organic layer was dried over anhydrous sodium sulfate, the solvent was distilled off and precipitated crystals were washed with heptane to obtain 0.64 g (yield 32%) of compound (II).

Example C-5

6.02 g (63.0 mmol) of guanidine hydrochloride was added to 12.2 g (63.0 mmol) of 28% sodium methoxide (methanol solution), then 2.60 g (10.5 mmol) of hexachloropropene was dropwise added thereto over a period of one hour under reflux. The reaction was conducted further for one hour, then methanol was distilled off, 20 g of methylisobutylketone and 20 g of water were added, and the organic layer was separated. The organic layer was dried over anhydrous sodium sulfate, the solvent was distilled off and precipitated crystals were washed with heptane to obtain 0.66 g (yield 33%) of compound (II).

Example C-6

A solution containing 2.52 g (63.0 mmol) of sodium hydroxide dissolved in 12.6 g of methanol was dropwise added into a mixture of 1.00 g (10.5 mmol) of guanidine hydrochloride, 2.60 g (10.5 mmol) of hexachloropropene and 3.0 g of methanol over a period of one hour under reflux. The reaction was conducted for one hour, methanol was distilled off, 20 g of methylisobutylketone and 20 g of water were added, and the organic layer was separated. The organic layer was dried over anhydrous sodium sulfate, the solvent was distilled off, whereupon precipitated crystals were washed with heptane to obtain 0.56 g (yield 28%) of compound (II).

Example C-7

1.20 g (12.6 mmol) of guanidine hydrochloride was added to 3.70 g of 95% sodium methoxide and 10.0 g of diethylene glycol dimethyl ether, followed by heating at a temperature of 60° C. for one hour. After the reaction solution was cooled to −10° C., the mixed solution of 2.60 g of hexachloropropene and 5 g of diethylene glycol dimethyl ether was dropwise added thereto at a temperature of at highest 0° C., and the reaction was conducted for one hour. It was confirmed that in this reaction solution, 0.80 g (yield 40%) of the desired compound (II) in the internal standardization amount exists.

Example C-8

1.20 g (12.6 mmol) of guanidine hydrochloride was added to 3.70 g of 95% sodium methoxide and 20.0 g of diethylene glycol dimethyl ether, followed by heating at a temperature of 60° C. for one hour, and then 5 g of diethylene glycol dimethyl ether was distilled off. The reaction solution was cooled to −10° C., then a mixed solution of 2.60 g of hexachloropropene and 5 g of diethylene glycol dimethyl ether was dropwise added thereto at a temperature of at highest 0° C., and the reaction was conducted for one hour. It was confirmed that in this reaction solution, 1.00 g (yield 50%) of the desired compound (II) in the internal standardization amount exists.

Example C-9

1.20 g (12.6 mmol) of guanidine hydrochloride was added to 3.70 g (65.1 mmol) of 95% sodium methoxide and 10.0 g of 1-methyl-2-pyrrolidinone, followed by heating at a temperature of 60° C. for one hour. The reaction solution was cooled to −10° C., then a mixed solution of 2.60 g (10.5 mmol) of hexachloropropene and 5 g of 1-methyl-2-pyrrolidinone, was dropwise added thereto at a temperature of at highest 0° C, and the reaction was conducted for one hour. It was confirmed that in this reaction solution, 0.80 g (yield 40%) of the desired compound (II) in the internal standardization amount exists.

Example C-10

1.20 g (12.6 mmol) of guanidine hydrochloride was dissolved in 10.0 g of methanol, and 2.63 g (65.1 mmol) of 99% sodium hydroxide was added thereto, followed by reaction for one hour. Methanol was distilled off at a temperature of 40° C., 20.0 g of diethylene glycol dimethyl ether was added thereto, among which 5.0 g of diethylene glycol dimethyl ether was distilled off. Then the mixture was cooled to −10° C. and 2.60 g (10.5 mmol) of hexachloropropene was dropwise added over a period of 30 minutes, and the reaction was conducted for one hour. It was confirmed that in this reaction solution, 0.40 g (yield 20%) of the desired compound (II) in the internal standardization amount exists.

Example C-11

2.63 g (65.1 mmol) of 99% sodium hydroxide was added to a mixture of 1.00 g (10.5 mmol) of guanidine hydrochloride, 2.60 g (10.5 mmol) of hexachloropropene and 10.0 g of methanol at a temperature of 50° C. over a period of 30 minutes. After the reaction was conducted for one hour, methanol was distilled off, 20 g of toluene and 20 g of water were added, and the organic layer was separated. The organic layer was dried over anhydrous sodium sulfate, the solvent was distilled off and precipitated crystals were washed with heptane to obtain 0.16 g (yield 8%) of compound (II).

Production Method D

Example D-1

A mixture of 1.00 g (5.15 mmol) of compound (III), 1.98 g (10.3 mmol) of 28% sodium methoxide (methanol solution) and 6 g of methanol was refluxed for three hours. After the reaction, methanol was distilled off and 10 g of water was added to precipitate crystals. The crystals were subjected to filtration, washed with water and dried to obtain 0.88 g (yield 90%) of compound (II).

Example D-2

A mixture of 1.00 g (5.15 mmol) of compound (III), 0.42 g (10.3 mmol) of 28% sodium hydroxide and 9 g of methanol was refluxed for three hours. After the reaction, methanol was distilled off and 10 g of water was added to precipitate crystals. The crystals were subjected to filtration, washed with water and dried to obtain 0.93 g (yield 95%) of compound (II).

Production Method E

Example E-1

3.97 g (20 mmol) of compound (IV), 2.40 g (60 mmol) of sodium hydroxide and 40 ml of methanol were refluxed under heating for two hours. After the reaction, methanol was distilled off, 50 g of water was added, extraction with 50 g of methylisobutylketone was carried out, the organic layer was dried over anhydrous sodium sulfate and the solvent was distilled off to obtain 3.60 g (19 mmol) (yield 95%) of compound (II).

Example E-2

3.97 g (20 mmol) of compound (IV), 1.60 g (40 mmol) of sodium hydroxide and 40 g of methanol were charged into an autoclave and heated at a temperature of 120° C. for three hours. The internal pressure was 4.2 kg/cm$^2$. After cooling, the reaction solution was put into an eggplant type flask, methanol was distilled off under reduced pressure, 50 g of water was added thereto, and extraction with 100 g of ethyl acetate was carried out. After the organic layer was washed with a sodium hydroxide aqueous solution and washed with water then dried over anhydrous sodium sulfate, the solvent was distilled off to obtain 3.41 g (18 mmol) (yield 90%) of compound (II). Besides, 6.5% of compound (III) was produced.

Example E-3

3.24 g (60 mmol) of sodium methoxide was added to 3.97 g (20 mmol) of compound (IV) and 50 ml of methanol under stirring at room temperature, followed by stirring at room temperature for one hour. After the reaction, methanol was distilled off, 50 g of water was added, extraction with 20 g of methylisobutylketone was carried out. The organic layer was dried over anhydrous sodium sulfate, and the solvent was distilled off to obtain 3.52 g (18.6 mmol) (yield 93%) of compound (II).

Example E-4

3.97 g (20 mmol) of compound (IV), 3.37 g (60 mmol) of potassium hydroxide and 40 ml of methanol were refluxed under heating for two hours. After the reaction, methanol was distilled off, 50 g of water was added, extraction with 20 g of methylisobutylketone was carried out, the organic layer was dried over anhydrous sodium sulfate, and the solvent was distilled off to obtain 3.60 g (19 mmol) (yield 95%) of compound (II).

Example E-5

3.97 g (20 mmol) of compound (IV), 1.60 g (40 mmol) of barium hydroxide octahydrate and 40 g of methanol were charged into an autoclave and heated at a temperature of 120° C. for three hours. The internal pressure was 4.2 kg/cm$^2$. After cooling, the reaction solution was put into an eggplant type flask, methanol was distilled off under reduced pressure, 50 g of water was added thereto, followed by acidification with acetic acid, and extraction with 100 g of methylisobutylketone was carried out. The organic layer was washed with a sodium hydroxide aqueous solution and washed with water then dried over anhydrous sodium sulfate, the solvent was distilled off to obtain 3.41 g (18 mmol) (yield 90%) of compound (II). Besides, 6.5% of compound (III) was produced.

Production Method F

Example F-1

3.97 g (20 mmol) of compound (IV), 3.17 g (30 mmol) of sodium carbonate and 40 ml of methanol were refluxed under heating for three hours. The reaction mixture was evaporate to dryness under reduced pressure, 50 ml of water was added thereto followed by stirring well, and crystals were subjected to filtration. Then, the crystals were washed with toluene and dried to obtain 3.61 g (yield 93%) of compound (III). Melting point: 198.3° C.–203.3° C.

$^1$H-NMR δ (ppm) [DMSO-d$_6$, δ]:3.95 (3H,s), 7.20 (2H, bs)

Example F-2

3.97 g (20 mmol) of compound (IV), 1.60 g (40 mmol) of potassium carbonate and 40 g of methanol were charged into an autoclave and heated at a temperature of 100° C. for two hours. After cooling, the same treatment as in Example 1 was conducted to obtain 3.00 g of crude compound (III). As a result of analysis, it was confirmed that the product contained 80% of compound (III) and 20% of compound (II) (liquid chromatography relative area).

Example F-3

3.97 g (20 mmol) of compound (IV), 8.00 g (80 mmol) of potassium hydrogencarbonate and 40 ml of methanol were refluxed under heating for three hours. After cooling, the reaction solution was analyzed by high-performance liquid chromatography and was confirmed to contain 82% of compound (III) by relative area.

INDUSTRIAL APPLICABILITY

According to the method of the present invention, 2-amino-4,6-dimethoxypyrimidine useful as an intermediate for drugs and pesticides, particularly as an intermediate for pesticides (disclosed in JP-A-59-122488, JP-A-61-210084 and JP-A-60-208977), its starting material 2-amino-5-chloro-4,6-dimethoxypyrimidine and its intermediate 2-amino-4,5-dichloro-6-methoxypyrimidine can be easily produced, and the present invention is highly useful.

What is claimed is:

1. A method for producing 2-amino-4,6-dimethoxypyrimidine, comprising:

reacting 2-amino-5-chloro-4,6-dimethoxypyrimidine with a hydrogen donor using a metal catalyst selected from the group consisting of nickel catalyst, palladium catalyst and platinum catalyst.

2. The method according to claim 1, wherein the 2-amino-5-chloro-4,6-dimethoxypyrimidine is obtained by reacting 1,1,1,2,2,3,3-heptachloropropane, 1,1,1,2,3,3,3-heptachloropropane or hexachloropropene with guanidine or a salt thereof, in the presence of an alkali metal hydroxide, an alkaline earth metal hydroxide, an alkali metal methoxide or an alkaline earth metal methoxide.

3. The method according to claim 1, wherein the 2-amino-5-chloro-4,6-dimethoxypyrimidine is obtained by reacting 2-amino-4,5-dichloro-6-methoxypyrimidine with methanol in the presence of an alkali metal hydroxide, an alkaline earth metal hydroxide, an alkali metal methoxide or an alkaline earth metal methoxide.

4. The method according to claim 3, wherein the 2-amino-4,5-dichloro-6-methoxypyrimidine is obtained by reacting 2-amino-4,5,6-trichloropyrimidine with methanol in the presence of an alkali metal carbonate, an alkali metal hydrogencarbonate, an alkaline earth metal carbonate or an alkaline earth metal hydrogencarbonate.

5. The method according to claim 1, wherein the 2-amino-5-chloro-4,6-dimethoxypyrimidine is obtained by reacting 2-amino-4,5,6-trichloropyrimidine with methanol in the presence of an alkali metal hydroxide, an alkaline earth metal hydroxide, an alkali metal methoxide or an alkaline earth metal mechoxide.

6. A method for producing 2-amino-4,6-dimethoxypyrimidine, comprising:

reacting 1,1,1,3,3,3-hexachloropropane or 1,1,3,3,3-pentachloropropene with guanidine or a salt thereof, in the presence of an alkali metal hydroxide, an alkaline earth metal hydroxide, an alkali metal methoxide or an alkaline earth metal methoxide.

7. A method for producing 2-amino-5-chloro-4,6-dimethoxypyrimidine, comprising:

reacting 1,1,1,2,2,3,3-heptachloropropane, 1,1,1,2,3,3,3-heptachloropropane or hexachloropropene with guanidine or a salt thereof, in the presence of an alkali metal hydroxide, an alkaline earth metal hydroxide, an alkali metal methoxide or an alkaline earth metal methoxide.

8. The method of claim 1, wherein said contacting is conducted in the presence of a base.

9. The method of claim 1, wherein said contacting is conducted in the absence of a base.

* * * * *